United States Patent [19]

Hicks

[11] Patent Number: 4,631,300
[45] Date of Patent: Dec. 23, 1986

[54] PROCESS FOR PREPARING LOW VISCOSITY UV CURABLE POLYACRYLATES

[75] Inventor: Darrell D. Hicks, Jeffersontown, Ky.

[73] Assignee: Interez, Inc., Louisville, Ky.

[21] Appl. No.: 773,978

[22] Filed: Sep. 9, 1985

Related U.S. Application Data

[60] Continuation-in-part of Ser. No. 663,286, Oct. 22, 1984, which is a division of Ser. No. 488,317, Apr. 25, 1983, Pat. No. 4,511,732, which is a continuation-in-part of Ser. No. 357,960, Mar. 15, 1982, abandoned.

[51] Int. Cl.⁴ .................. C08L 63/10; C07C 67/08
[52] U.S. Cl. .................. 522/100; 560/90; 560/199; 560/221; 560/224; 525/DIG. 922
[58] Field of Search .................. 560/221, 224, 90, 199; 204/159.23; 522/100

[56] References Cited

U.S. PATENT DOCUMENTS

| | | | |
|---|---|---|---|
| 2,890,202 | 6/1959 | Parker | 528/114 |
| 4,025,548 | 5/1977 | Huemmer et al. | 560/224 |
| 4,164,423 | 8/1979 | Schumacher et al. | 522/71 |

FOREIGN PATENT DOCUMENTS 2453874  5/1975  Fed. Rep. of Germany .

OTHER PUBLICATIONS

Noller, Carl R. *Chemistry of Organic Compounds* (1957) 2nd Ed. W. B. Saunders, Publ. 744–5.

*Primary Examiner*—Natalie Trousof
*Assistant Examiner*—L. Hendriksen
*Attorney, Agent, or Firm*—Lynch, Sherman & Cox

[57] ABSTRACT

Photocurable polyacrylate or methacrylate compounds which exhibit extremely low, neat viscosities while at the same time maintaining the high cure response of other related photocurable materials may be represented by the general formula:

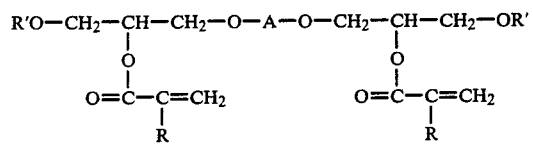

wherein R is hydrogen or methyl, R' is $C_1$–$C_8$ alkyl or $C_3$–$C_8$ alkyl ether alkyl and A is the residue of a diol or dicarboxylic acid, preferably, a diphenol such as Bisphenol A. The process for preparing these materials involves reacting a $C_1$–$C_8$ aliphatic alcohol or $C_3$–$C_8$ aliphatic ether alcohol with a diglycidyl ether or ester and esterifying the remaining hydroxyl groups with acrylic or methacrylic acid.

5 Claims, No Drawings

PROCESS FOR PREPARING LOW VISCOSITY UV CURABLE POLYACRYLATES

CROSS REFERENCE TO RELATED APPLICATIONS

This is a continuation-in-part of application Ser. No. 663,286, field Oct. 22, 1984, which is a division of application Ser. No. 488,317, filed Apr. 25, 1983, now Patent No. 4,511,732, which is a continuation-in-part of application Ser. No. 357,960, filed Mar. 15, 1982, and now abandoned.

BACKGROUND OF THE INVENTION

This invention relates to epoxide-based photocurable compositions and to processes for preparing these compositions. More particularly this invention relates to polyacrylate- or methacrylate-containing photocurable monomers which are of relatively low viscosity and yet possess a cure response equivalent to other epoxide-based photocurable monomers.

For many years it has been known to prepare polyacrylic- or methacrylic-based monomers by reacting acrylic or methacrylic acid with a polyglycidyl ether, such as the diglycidyl ether of Bisphenol A. Examples of patents which involve the use of these compositions in photocurable systems include U.S. Pat. Nos. 4,072,592; 3,676,398 and 3,770,602. In addition, in at least one instance in the prior art, a polyglycidyl ether has been reacted with a polyol or a polyol ether and the resulting product reacted with acrylic acid or methacrylic acid. See U.S. Pat. No. 2,890,202, issued June 9, 1959. However, the product disclosed in this patent is not shown to be useful as a photocurable monomer.

The polyacrylic or methacrylic esters of polyglycidyl ethers have been particularly useful in protective coatings because of their rapid cure rates, high degree of toughness and good chemical resistance. However, their extremely high, neat viscosity has been a serious drawback, particularly in those photocurable systems where the presence of a solvent would significantly reduce the cure time of the system. Because nearly all acrylic or methacrylic esters of polyglycidyl ethers are resinous and of extremely high viscosity, often approaching 5,000,000 cps, it is virtually impossible to use these materials without at least employing some solvent or diluent.

Thus, it is an object of this invention to prepare photocurable monomers which are acrylate or methacrylate esters of polyglycidyl-containing compounds.

It is another object of this invention to prepare such acrylic or methacrylic esters having viscosities sufficiently low to allow their use in essentially 100% solids photocurable systems without the necessity of employing diluents or solvents.

It is another object of this invention to prepare photocurable compositions which are of low viscosity, but at the same time maintain the relatively high degree of cure rate present in prior art acrylic or methacrylic esters of polyglycidyl ethers.

These and other objectives are obtained by preparing the compositions of the instant invention.

SUMMARY OF THE INVENTION

Basically, the compositions of the instant invention are represented by the general formula:

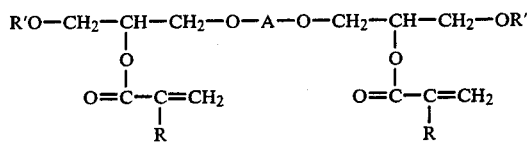

wherein R is hydrogen or methyl, R' is $C_1$–$C_8$ alkyl or $C_3$–$C_8$ alkyl ether alkyl, and A is the aromatic or aliphatic residue of a diol or the diacyl aliphatic or aromatic residue of a dicarboxylic acid. The compositions of this invention in their preferred state may be described as the dialkyl ether of the diacrylate ester of the diglycidyl ether of a dihydric phenol. In addition, this invention involves a novel process for preparing these compounds, which comprises reacting an aliphatic alcohol or aliphatic ether alcohol with a diepoxide compound, i.e., a diglycidyl ether or ester and esterifying the secondary hydroxyl group which result with acrylic or methacrylic acid. The diglycidyl ether or ester can be represented by the formula:

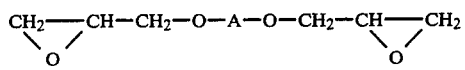

wherein A has the same definition as described in the Summary of the Invention.

DETAILED DESCRIPTION OF THE INVENTION

The diepoxide compounds useful in the instant invention are diepoxides prepared from aliphatic or aromatic diols or dicarboxylic acids. The polyepoxide materials must contain terminal epoxide groups of the 1,2 or vicinal type.

The aromatic diol based diepoxides are glycidyl polyethers of dihydric phenols having more than one up to two 1,2-epoxide groups per molecule. These materials are prepared by reacting a dihydric phenol with an epihalohydrin and have epoxide equivalent weights of about 110 to about 350. Examples of useful epihalohydrins are epichlorohydrin, epibromohydrin and epiiodohydrin with epichlorohydrin being preferred. The aromatic diols (dihydric phenols) from which these glycidyl polyethers are derived are exemplified by resorcinol, hydroquinone, p,p'-dihydroxydiphenyl propane, or Bisphenol A as it is commonly called, p,p'-dihydroxybenzophenone, p,p'-dihydroxybiphenyl, p,p'-dihydroxydiphenyl ethane, p,p'-dihydroxydiphenyl methane, bis(2-hydroxynaphthyl) methane, 1,5-dihydroxynaphthalene and the like. Preferably, these glycidyl polyethers are prepared by reacting epihalohydrin in an amount at least equal to the phenolic hydrogens, and, most preferably, in excess, in the presence of an alkali metal hydroxide sufficient to dehydrohalogenate the reaction product. The preparation of glycidyl polyethers of dihydric phenols is described in U.S. Pat. Nos. 2,467,171 and 2,801,227 which are incorporated herein by reference.

The aliphatic diol based diepoxides are prepared by reacting the diol with an epihalohydrin forming a halohydrin ether which is the dehydrohalogenated with an alkali metal hydroxide. The preparation of such diepoxides is described in U.S. Pat. No. 3,033,803 which is incorporated herein by reference. Examples of the aliphatic diols useful in preparing these diepoxides include ethylene glycol, propylene glycol, 1,4-butanediol, 1,5-pentanediol, 1,4-hexanediol, 2-ethylhexanediol-1,6,hydrogenated Bisphenol A, 1,4-cyclohexanediol, 1,3-cyclopentanediol, cyclohexanedimethanol, and the like.

The dicarboxylic acid based polyepoxides useful in this invention are glycidyl polyesters prepared by reacting an epihalohydrin, preferably, epichlorohydrin, with an aliphatic or aromatic dicarboxylic acid and then dehydrohalogenating the resulting halohydrin ester with an alkali metal hydroxide. The preparation of such diglycidyl esters is described in U.S. Pat. No. 3,859,314 which is incorporated herein by reference. Examples of dicarboxylic acids useful in preparing these glycidyl esters include oxalic acid, sebacic acid, adipic acid, succinic acid, pimelic acid, suberic acid, glutaric acid, dimer acids of unsaturated fatty acids, phthalic acid, isophthalic acid, terephthalic acid, hexahydrophthalic acid, tetrahydrophthalic acid and the like.

Referring to the formula

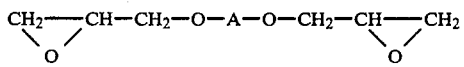

A is an aromatic diol, an aliphatic diol, or a dicarboxylic acid minus the two OH groups which is part of the diol or diacid.

The second important component of the instant invention is a $C_1$-$C_8$ aliphatic alcohol or $C_3$-$C_8$ aliphatic ether alcohol. Examples of the aliphatic alcohols include the methyl, ethyl, n-propyl, isopropyl, n-butyl, 2-ethylhexyl, and allyl alcohols. In addition, the alcohols may be either primary, secondary, or tertiary. However, the primary alcohols are preferred. The aliphatic ether alcohols are exemplified by the various glycol monoethers, such as monomethylether of ethylene glycol, monoethylether of ethylene glycol, monobutylether of ethylene glycol, monomethylether of propylene glycol, monoethylether of propylene glycol, monobutylether of butylene glycol, monomethylether of diethylene glycol. These aliphatic ether alcohols contain three to eight carbon atoms, one to two ether groups and one aliphatic hydroxyl group.

In preparing the compositions of this invention, the particular aliphatic alcohol which is chosen is dependent upon the particular end use selected. For example, if a hard, tough film is desired, the lower aliphatic alcohols, such as the methyl or ethyl alcohols, should be used. However, if softer, more pliable films are desired, the higher carbon-containing alcohols, such as, for example, 2-ethylhexyl alcohol, is chosen. In addition, mixtures of the various alcohols may be employed to obtain products having particularly desired characteristics.

The final component of this invention is the acrylic acid ester or methacrylic acid ester, with the acrylic acid ester being the most photo-reactive, and accordingly the most preferred.

In preparing the compositions of this invention, it is usual to react the diepoxide and the aliphatic monoalcohol utilizing about 0.05 to about 2.0 percent by weight, based on the total reaction mixture, preferably, 0.1 to about 1.0 percent by weight, of a Lewis acid catalyst. Examples of the catalyst include boron trifluoride (and its diethyl ether complex), ferric chloride and tin chloride.

This reaction may be carried out at any temperature ranging from ambient temperatures up to about 80° C. or more, preferably, about 60°-80° C., depending upon the reactivity of the various components. The preferred reaction temperature is the minimum temperature at which the reaction will proceed readily and rapidly. The reaction is carried out by adding one equivalent of the diepoxide to a relatively large excess of the alcohol mixed with the Lewis acid catalyst. The epoxide is added over, preferably, about one to four hours. The ratio of the equivalents of epoxide to the equivalents of alcohol will vary from about ⅓ to 1/5 or higher. If less than 3 equivalents of alcohol are used per equivalent of epoxide, the etherification reaction can be carried to completion with no problem. However, in the subsequent esterification reaction with acrylic or methacrylic acid, the resulting esterification reaction product gels before the esterification reaction is complete, or during the removal of solvent and workup of the product. More than 5 equivalents of alcohol can be used per epoxide equivalent, up to 10 or even higher. However, from a practical standpoint, 5 equivalents are generally sufficient. After this etherification reaction is completed, as measured by the complete disappearance of epoxide groups in the reaction mixture, the excess alcohol is removed by distillation, preferably, under vacuum.

Following the formation of this diether, it is mixed with acrylic or methacrylic acid in the ratio of about one equivalent or acrylic or methacrylic acid for each hydroxyl equivalent (two per mole) in the polyether. In addition to the acrylic or methacrylic acid and the diether, about 0.1 to about 3.0 percent, based on the total reaction mixture, of a polymerization inhibitor is added to the mixture in order to reduce or eliminate the possibility of polymerization during the esterification reaction. Examples of such materials include the quinones, such as hydroquinone and its monomethylether, the various phenols, p-tert-butylcatechol, p-methoxyphenol, 2,4-dichloro-6-nitrophenol, n-propyl gallate, di-tert-butyl-p-cresol, 2,2'-methylenebis(4-methyl-6-tert-butylphenol), 1-amino-7-naphthol, p-benzoquinone, 2,6-dichloro-p-benzoquinone, 2-amino-1,4-naphthoquinone, 3-aminoanthraquinone, diphenylamine, nitrobenzene, phenothiazine, N-nitrosodimethylamine, hexamethylphosphoramide, n-dodecyl mercaptan, benzenethiol, 2,2-diphenyl-1-picrylhydrazyl (phenyl hydrazine), divinylacetylene, and various antimony and copper salts. Most preferred among the inhibitors are paramethoxyphenol, hydroquinone and its monomethylether, phenothiazine and nitrobenzene.

Also added to the mixture is an esterification catalyst of conventional type. The esterification catalyst should be added in the range of about 1–10 percent, preferably, 1–5 percent, based on the total amount of the reactants. The preferred esterification catalyst is para-toluene sulfonic acid (PTSA) or methane sulfonic acid, although the reaction may also be catalyzed utilizing a titanium ester, titanium chelate, or aluminum, bismuth, barium, zinc, copper, tin, chromium, calcium, antimony or cadmium, alcoholate, carboxylate, halide or alkyl oxide.

The final component of the esterification reaction mixture is a reflux/azeotrope solvent which is used to remove the water of esterification. Preferably the azeotrope solvent is one which produces an azeotrope so as to remove water at temperatures no higher than about 120° C. Examples of such solvents include, preferably, benzene and toluene, although xylene may also be used in certain instances. The amount of the reflux solvent which is added may vary. However, generally it will be added in the range of about 30 to about 150 percent, based on the total weight of the reaction mixture. The reaction itself is carried out over several hours utilizing an air sparge to activate the polymerization inhibitor. The reaction is monitored by measuring the acid value of the reaction mixture, taking into account, of course, any acid value added by the reaction catalyst itself. After the reaction is completed, the azeotrope solvent is removed by distillation, preferably, under vacuum.

The esterification catalyst may be removed from the reaction medium by means of a cation exchange resin. This resin may be added directly to the reaction mixture and then filtered off, or the finished product may be passed through a cation exchange column. The preferred type of cation exchange resin is of the tertiary amine type. In the alternative, the insoluble salt of the reaction catalyst is formed such as by adding ammonia to a PTSA catalyst system. The reaction mixture is then filtered to remove the salted catalyst.

The compositions prepared above may be utilized in photocurable coating compositions as the only curable material. They may also be blended with up to about 95 percent by weight, based on the total curable composition, of another alpha beta ethylenically unsaturated vinyl polymerizable compound containing two or more vinyl polymerizable groups per molecule. Examples of these materials are set forth in U.S. Pat. No. 4,207,155. In addition, the photocurable compositions may contain compounds having a single polymerizable ethylenically unsaturated group of the acrylate, methacrylate, or vinyl type, all as disclosed in the aforementioned U.S. patent. Also the compositions of the instant invention may be compounded with polymeric materials containing no polymerizable unsaturation, as well as with immiscible polymeric or nonpolymeric, organic or inorganic fillers or reinforcing agents in varying amounts.

The compositions of the instant invention are useful in photocurable systems and may be cured by ultraviolet light, electron beam, or any other type of system which utilizes photons to activate the polymerization of the unsaturated materials prepared herein.

The compositions of this invention can be applied by conventional means, including brushing, spraying, dipping, curtain and roll coating techniques, and may, if desired, be dried under ambient or oven conditions.

In order to render the compositions of the instant invention photocurable, it is common to employ photosensitizers, such as benzoin, acetophenone, alkylphenone, benzophenone, tricyclic fused ring, pyridal, and the like, all as disclosed in U.S. Pat. No. 4,207,155. The photosensitizers are added to the compositions in amounts ranging from about 0.1 to about 15.0 percent by weight, based on the total curable system, preferably, about 1.0 to about 5.0 percent. Although not required, certain organic amine-type activators may be added to these compositions to further enhance the cure rate in amounts ranging up to about 500 percent by weight, based on the photosensitizer, preferably, up to about 50 percent by weight. The amines are further described in the above patent.

In the following examples, all parts and percentages are by weight unless otherwise indicated.

EXAMPLE 1

Into a reactor equipped with a mechanical agitator, thermometer, sampling tube and reflux condenser were added 800 parts of methanol and 3.8 parts of boron trifluoride etherate. The materials were heated to a temperature of 57° C. and maintained at a temperature of 68° C., while 945 parts of Epi-Rez 510 were added over a 25 minute period. (Epi-Rez 510 is a diglycidyl ether of Bisphenol A having a weight per epoxide of about 190, available from Celanese Specialty Resins, a division of Celanese Corporation.) The resulting reaction mixture had a hydroxyl/epoxide equivalent ratio of 5/1. The reaction mixture was maintained at a temperature of 68° C. for approximately 2 hours, at which time a distillation condenser was added and a vacuum of 30-40 mm Hg was applied. The temperature was gradually increased to 100° C. to remove the excess methanol under a vacuum of 1-2 mm Hg.

To 1098 parts of the resulting product were added 357 parts of acrylic acid, 1455 parts of toluene, 63 parts of paratoluene sulfonic acid monohydrate, and 14.6 parts of hydroquinone monomethylether. The material was then heated to 106° C., at which time water began refluxing over. The material was heated for approximately 10 hours 15 minutes at a temperature ranging from 106° C. to 115° C. until an acid value of 10.3 was obtained and 99 parts of water had been removed. The material was then passed through an ion exchange column employing Amberlyst A-21 ion exchange resin to remove the para-toluene sulfonic acid. (Amberlyst A-21 is a weakly basic, anion, tertiary amine, exchange resin, available from the Rohm & Haas Company). The resulting product had an acid value of 0.68. Utilizing a vacuum down to 1-2 mm Hg and heat ranging up to 78° C. over an approximately two and one-half hour period, the toluene was removed. The resulting product exhibited a solids content of 96.1%, an acid value of 0.8, a Gardner-Holdt 25° C. viscosity of $Z_6$-$Z_7$, and a color of 7-8.

EXAMPLES 2 THROUGH 5

Utilizing Epi-Rez 510, acrylic acid and the terminating alcohol indicated below, the following essentially the same procedures specified in Example 1, the following additional products were prepared:

| Example | | Solids | Color | Acid Value | Gardner-Holdt 25° C. Viscosity |
|---|---|---|---|---|---|
| 2 | allyl | 97.9 | 11-12 | 0.9 | $Z_6$-$Z_7$ |
| 3 | n-butyl | 97.4 | 5-6 | 0.9 | $Z_2$ |
| 4 | 2-ethylhexyl | 99.3 | 6-7 | 1.5 | $Z_6$-$Z_7$ |
| 5 | ethylene glycol monomethylether | 99.3 | 12-13 | 1.6 | $Z_7$ |

EXAMPLE 6

468 parts of the diacrylate ester of a diglycidyl ether of Bisphenol A were placed in a reactor equipped with a mechanical agitator, thermometer, sampling device and distillation condenser. (The material known as Celrad 3700, available from Celanese Specialty Resins, a division of Celanese Corporation, has a molecular weight of 524, a typical viscosity at 25° C. of 1,000,000 cps, a specific gravity of 1.2, and an acid value of 2.) Added to this material were 132 parts of propionic acid, 26.9 parts of para-toluene sulfonic acid monohydrate, 6.0 parts of hydroquinone monomethylether, and 600 parts of toluene. The mixture was refluxed at temperatures ranging from 101°-115° C. for approximately 3 hours, after which time the material was passed through the ion exchange column described in Example 1, yielding a product which exhibited an acid value of 0.4. The toluene was then removed by distillation under 22 mm Hg vacuum at temperatures ranging from 85° C. to 124° C. A product resulted which exhibited a solids content of 98.2%, an acid value of 10.7 and a Gardner-Holdt viscosity at 80% solids in Cellosolve acetate of Y-Z. For comparison purposes, the viscosity of Celrad 3700, the starting material, is essentially the same, W-X at 80% solids in ethylene glycol monoethyl ether acetate. The neat material, however, was a viscous liquid having a viscosity too high to measure accurately at 25° C.

When this material, which is the lower alkyl ester of the diacrylate ester of the diglycidyl ether of Bisphenol A, is compared to the corresponding ethers prepared in Examples 1-5, is marked and surprising difference in viscosity is noted. The ether materials, as opposed to the ester materials, are of extremely low viscosity and easily handleable at room temperatures and 100% solids, while the corresponding ester is not.

Each of the above materials cured to a tack-free protective coating when blended with conventional ultraviolet curing catalysts applied to a substrate and subject to ultraviolet radiation.

EXAMPLE 7

To a reactor equipped as described in Example 1 were added 740 parts of n-butanol. Heat was applied raising the temperature to 60° C. Boron trifluoride etherate, 1.5 parts, was added and slow addition of 380 parts of Epi-Rez 510 was begun. All of the Epi-Rez 510 was added over a period of 1 hour and 20 minutes with the temperature being controlled between 60° C. and 71° C. The reactants had a hydroxyl to epoxide equivalent ratio of 5/1. The temperature was then raised to 100° C. and was held at 100° C. for 30 minutes. Water, 5 parts, was added, the reactor was fitted with a distillation condenser and vacuum was applied to distill off the unreacted butanol. The initial pressure was 33 mm Hg. The pressure was slowly reduced to 1.9 mm Hg with the pot temperature being raised to 145° C. over a period of 3 hours and 40 minutes. The resulting dibutyl ether of Epi-Rez 510 was recovered in the amount of 525 parts.

To 454.6 parts of the above product were added 121.7 parts of acrylic acid, 26 parts of para-toluene sulfonic acid monohydrate, 5.76 parts of hydroquinone monomethyl ether and 576 parts of toluene. The components were heated to 110° C. at which point water began refluxing over. Heating was continued for 5 hours and 35 minutes with the temperature gradually rising to 117° C. The acid value at the end of this heating period was 15.2. The material was then passed through an ion exchange resin using Amberlyst A-21 ion exchange resin. The resulting material had an acid value of 0.28. The toluene was then removed by distillation under vacuum. The resulting product, 512.5 parts, had a Gardner-Holdt viscosity at 25° C. of $Z_3$-$Z_4$, a Gardner color of 10-11, an acid value of 1.1 and % solids of 97.52.

EXAMPLE 8

Using the same procedure as described in Example 7, 380 parts of Epi-Rez 510 were reacted with 444 parts of n-butanol and 1.5 parts of boron trifluoride etherate. The hydroxyl to epoxide equivalent ratio was 3/1. After removal of the unreacted n-butanol, 512.2 parts of the ether product were recovered.

The ether product, 512.2 parts, was esterified with 136.9 parts of acrylic acid using 29.45 parts of para-toluene sulfonic acid monohydrate as esterification catalyst, 6.49 parts of hydroquinone monomethyl ether as polymerization inhibitor and 649.1 parts of toluene as solvent. After 6 hours heating at 107°-116° C., the resulting product was passed through an ion exchange column and the toluene solvent was removed by distillation. The resulting product, 575.8 parts, had a Gardner-Holdt viscosity at 25° C. of $Z_5$-$Z_6$, a Gardner color of 5-6, an acid value of 1.1 and % solids of 97.4.

EXAMPLE 9

Using the same procedure described in Example 7, 380 parts of Epi-Rez 510 were reacted with 296 parts of n-butanol and 1.5 parts of boron trifluoride etherate. The hydroxyl to epoxide equivalent ratio was 2/1. After removal of the unreacted n-butanol, 502.6 parts of the ether product were recovered.

The ether product, 502.6 parts, was esterified with 134.4 parts of acrylic acid using 28.89 parts of para-toluene sulfonic acid monohydrate, 6.37 parts of hydroquinone monomethyl ether and 637 parts of toluene. After heating for 6 hours at 114°-116° C., the resulting product had an acid value of 11.6. After passing through an ion exchange column, the acid value was 0.48. The reactor was fitted with a distillation condenser for vacuum distillation to remove the toluene solvent. The toluene was removed under 16 mm Hg pressure to a pot temperature of 123° C. Before all of the toluene could be removed, the product gelled and was discarded.

EXAMPLE 10

To 100 parts of the dibutyl ether of Epi-Rez 510, prepared as described in Example 7, were added 37.6 parts of maleic anhydride and 0.69 parts of triethylamine. The reactants were heated for 2 hours and 9 minutes at 111°-120° C. At the end of this heating period, 34.4 parts of methyl ethyl ketone were added to reduce the viscosity to a workable range.

To 12.5 parts of the above solution were added 0.3 parts of benzophenone and 0.2 part of methyl diethanolamine. Films were prepared from the resulting blend on steel panels using a #4 Meyer Bar. After flashing for 10 minutes, the coated panels were passed through a Fusion Ultraviolet Curing Unit, Model F-440, Fusion Systems Corporation, Rockville, Md., with two 300 watt per linear inch mercury vapor lamps at 60 feet per minute. The coatings exhibited no cure. The panels were given a second pass through the unit. No change was observed in the coatings; they remained very tacky.

The acrylic acid ester product, prepared as described in Example 7, was diluted with methyl ethyl ketone and blended with benzophenone and methyl diethanolamine in the same amounts as described above. Films were prepared on steel panels and were passed through the Ultraviolet Curing Unit as described above. After one pass the coatings were cured to a tack-free state, exhibiting 2 methyl ethyl ketone double rubs, 2 toluene double rubs and 3 methylisobutyl ketone double rubs.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing a liquid composition which in the presence of a photosensitizer is photopolymerizable which comprises:
   (a) reacting a $C_1$-$C_8$ aliphatic alcohol or a $C_3$-$C_8$ aliphatic ether alcohol with a diglycidyl ether of an aliphatic or aromatic diol or a diglycidyl ester of an aliphatic or aromatic dicarboxylic acid to produce a diether of the diglycidyl ether or ester wherein the diglycidyl ether or ester is added to an excess of the alcohol which contains a Lewis acid catalyst in the amount of about 0.05 to about 2.0 percent by weight, based on the total reaction mixture, and wherein at least 3 equivalents of alcohol are present for each equivalent of epoxide group;
   (b) removing the excess unreacted alcohol by distillation; and
   (c) reacting the diether of the diglycidyl ether or ester with acrylic acid or methacrylic acid in the presence of about 0.1 to about 3 percent by weight based on the total reaction mixture of a polymerization inhibitor and about 1 to about 10 percent by weight based on the total reaction mixture of an esterification catalyst at a temperature no higher than about 120° C. while removing the water of esterification as a solvent/washer azeotrope.

2. The process of claim 1 wherein the acid is acrylic acid and the diglycidyl ether is the diglycidly ether of p,p'-dihydroxydiphenyl propane.

3. The process of claim 1 wherein the aliphatic alcohol is methyl alcohol, ethyl alcohol, n-propyl alcohol, n-butyl alcohol, 2-ethylhexyl alcohol or allyl alcohol.

4. The process of claim 1 wherein the aliphatic ether alcohol is a glycol monoether.

5. A process for preparing a liquid photopolymerizable composition which comprises:
   (a) reacting at a temperature of about 60° C. to about 80° C. a $C_1$-$C_8$ aliphatic alcohol or a $C_3$-$C_8$ aliphatic ether alcohol with a diglycidyl ether of p,p'-dihydroxydiphenyl propane having an epoxide equivalent weight of about 190 to produce a diether of the diglycidyl ether wherein the diglycidyl ether is added to an excess of alcohol which contains boron trifluoride etherate in the amount of about 0.05 to about 2.0 percent by weight, based on the total reaction mixture, and wherein at least 3 equivalents of alcohol are present for each equivalent of epoxide group;
   (b) removing the excess unreacted alcohol by distillation;
   (c) reacting the diether of the diglycidyl ether with acrylic acid or methacrylic acid in the presence of about 0.1 to about 3 percent by weight based on the total reaction mixture of hydroquinone monomethyl ether and about 1 to about 10 percent by weight based on the total reaction mixture of para-toluene sulfonic acid at a temperature no higher than about 120° C. while removing the water of esterification as a toluene/water azeotrope; and
   (d) adding a photosensitizer.

* * * * *